United States Patent
Sakashita et al.

(10) Patent No.: US 9,442,129 B2
(45) Date of Patent: Sep. 13, 2016

(54) AUTOMATIC ANALYZER

(75) Inventors: Yukinori Sakashita, Hitachinaka (JP);
Katsuaki Takahashi, Hitachinaka (JP);
Tomoyuki Nemoto, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 305 days.

(21) Appl. No.: 13/982,745

(22) PCT Filed: Jan. 26, 2012

(86) PCT No.: PCT/JP2012/051619
§ 371 (c)(1),
(2), (4) Date: Oct. 14, 2013

(87) PCT Pub. No.: WO2012/105398
PCT Pub. Date: Aug. 9, 2012

(65) Prior Publication Data
US 2014/0037503 A1 Feb. 6, 2014

(30) Foreign Application Priority Data

Jan. 31, 2011 (JP) ................................ 2011-017385

(51) Int. Cl.
*G01N 35/10* (2006.01)

(52) U.S. Cl.
CPC ................................ *G01N 35/1004* (2013.01)

(58) Field of Classification Search
None
See application file for complete search history.

(56) References Cited

U.S. PATENT DOCUMENTS

| | | | | |
|---|---|---|---|---|
| 6,003,531 | A * | 12/1999 | Kimura | G01N 35/1004 134/155 |
| 6,815,198 | B2 * | 11/2004 | Nemoto | C12Q 1/6806 422/561 |
| 2008/0056942 | A1 * | 3/2008 | Arima | G01N 35/1004 422/63 |
| 2010/0051060 | A1 * | 3/2010 | Kuroda | G01N 35/1004 134/22.11 |
| 2011/0274584 | A1 * | 11/2011 | Kitamura | G01N 35/1004 422/63 |
| 2011/0293474 | A1 * | 12/2011 | Sugimura | G01N 35/1004 422/62 |
| 2012/0003731 | A1 * | 1/2012 | Kuroda | G01N 35/00732 435/288.7 |
| 2012/0227771 | A1 * | 9/2012 | Waterbury | G01N 35/1004 134/36 |

FOREIGN PATENT DOCUMENTS

| | | |
|---|---|---|
| JP | 06-207944 A | 7/1994 |
| JP | 10-062435 A | 3/1998 |

(Continued)

OTHER PUBLICATIONS

English translation of the International Preliminary Report on Patentability from International Application No. PCT/JP2012/051619, Aug. 6, 2013.

(Continued)

*Primary Examiner* — Jill Warden
*Assistant Examiner* — Benjamin Whatley
(74) *Attorney, Agent, or Firm* — Miles & Stockbridge P.C.

(57) ABSTRACT

An automatic analyzer cleans dispensing nozzles that dispense a sample or reagent using a rinse tank. The rinse tank includes first and second rinse liquid discharge ports arranged along the bottom and top of the rinse tank, respectively. The first rinse liquid discharge ports face the top of the rinse tank. The second rinse liquid discharge ports supply rinse liquid to flow to an exterior of the dispensing nozzles when aligned therewith. Each dispensing nozzle is rinsed by moving from a first position aligned with one of the first rinse liquid discharge ports to a second position aligned with one of the second rinse liquid discharge ports.

8 Claims, 3 Drawing Sheets

(56) References Cited

FOREIGN PATENT DOCUMENTS

| JP | 2005-241442 A | | 9/2005 |
|---|---|---|---|
| JP | 2005241442 A | * | 9/2005 |
| JP | 2009-041961 A | | 2/2009 |
| JP | 2010 085097 A | | 4/2010 |
| JP | WO 2010104072 A1 | * | 9/2010 ....... G01N 35/00732 |

OTHER PUBLICATIONS

European Search Report for related European Patent Application No. 12742716.9-1553 (mailed May 25, 2016).

* cited by examiner

AUTOMATIC ANALYZER

TECHNICAL FIELD

The present invention relates to analyzers that perform analyses using dispensing nozzles that suction and discharge given amounts of samples and reagents and particularly to an automatic analyzer having the function of rinsing dispensing nozzles used for dispensing samples and reagents.

BACKGROUND ART

As analyzers that use a sample and a reagent, have a mechanism for dispensing those into a reaction vessel, and detect the liquid that has reacted within the reaction vessel, there are various analyzers especially in the fields of medicine, biotechnology, and the like; for example, there is an automatic analyzer for detecting particular biological substances, chemical substances, and the like contained in a sample using blood, serum, urine, or the like as the sample. In this automatic analyzer, to achieve the realization of inspections having high accuracy and high reliability, further improvement in analysis accuracy is being attempted. Especially with a method of rinsing a dispensing nozzle, if the method is insufficient, the adsorbed substances may be detached, resulting in interfusion with another sample in next dispensing. This is generally called carryover and affects measurement results. Moreover, when only a small amount of a sample can be collected as children and the elderly, or to reduce patients' burden and the like, or to reduce the amounts of reagents used, the amounts of samples and reagents used will be further decreased from now on, and the tendency toward reduction in dispensation amounts of samples and reagents will be stronger. That is, more accurate dispensation of samples and reagents will be necessary than before. Coupled with the tendency toward reduction in dispensation amounts of samples and reagents, sufficient rinsing of dispensing nozzles used for dispensing samples and reagents is necessary for the prevention of carryover and contamination. For such problems, rinsing a dispensing nozzle using rinse water or rinse liquid is known, and various methods have been proposed. For example, the method disclosed in Patent Document (JP-1994-207944-A) is one in which a reagent vessel unit in which a reagent housing section for housing reagents and a rinse liquid housing section for housing rinse liquids used for the reagents are put together is housed within a reagent disk, a rinse tank for rinsing a dispensing nozzle is provided separately, the dispensing nozzle is temporarily moved onto the reagent disk to suction a rinse liquid, and the dispensing nozzle is then moved to the rinse tank to discharge the rinse liquid, thereby rinsing the dispensing nozzle.

PRIOR ART DOCUMENT

Patent Document

Patent Document 1: JP-1994-207944-A

SUMMARY OF THE INVENTION

Problems to be Solved by the Invention

According to Patent Document 1, it is the method in which a dispensing nozzle for dispensing, for example, a reagent suctions the reagent necessary for reaction from the reagent housing section, discharges into the a reaction vessel, moves to the reagent housing section again to suction a rinse liquid, then moves to a rinse tank to discharge the rinse liquid. However, when, for the purpose of rinsing the dispensing nozzle, the dispensing nozzle is moved to the reagent disk to suction a rinse liquid from the reagent vessel unit and the dispensing nozzle is moved to the rinse tank located away from the reagent disk to perform a rinse, it takes longer time to rinse, and the number of samples that can be measured within a given amount of time may be limited. As a result, processing capabilities may decrease.

It is an object of the present invention to rinse the inner and outer surfaces of a dispensing nozzle without reducing the processing speed of a device.

Means for Solving the Problems

To achieve the above object, a feature of the invention is that a dispensing nozzle rinse tank includes a rinse liquid supply port. More specifically, by suctioning rinse liquid from the rinse liquid supply port provided on the dispensing nozzle rinse tank and discharging the rinse liquid into the rinse tank, the inner and outer surfaces of the dispensing nozzle can be rinsed in a short amount of time.

Effects of the Invention

According to the invention, it is only required that a rinse liquid supply port be provided on a dispensing nozzle rinse tank, the structure is simple. Moreover, because the inner and outer surfaces of the dispensing nozzle can be rinsed in a short amount of time by shortening the movement distance of the dispensing nozzle, analyses can be performed without reducing the processing speed of the device.

MODE FOR CARRYING OUT THE INVENTION

Figure 1:
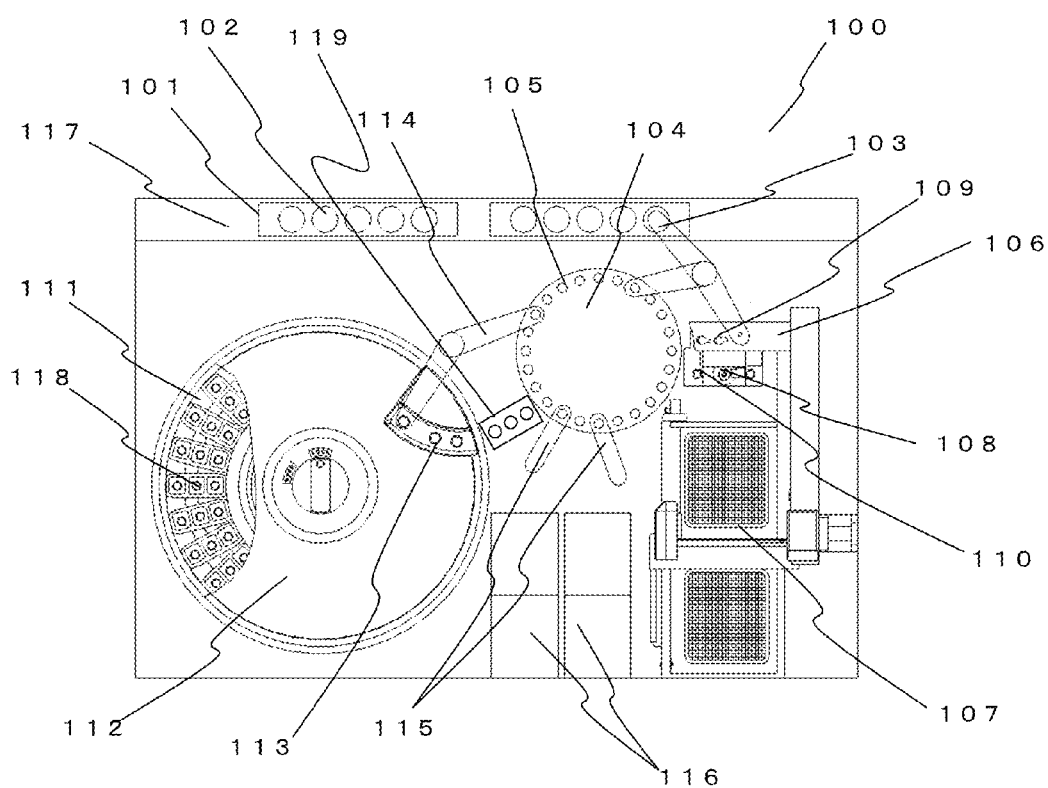
FIG. 1 illustrates an overall structure diagram of an automatic analyzer.
Figure 2:
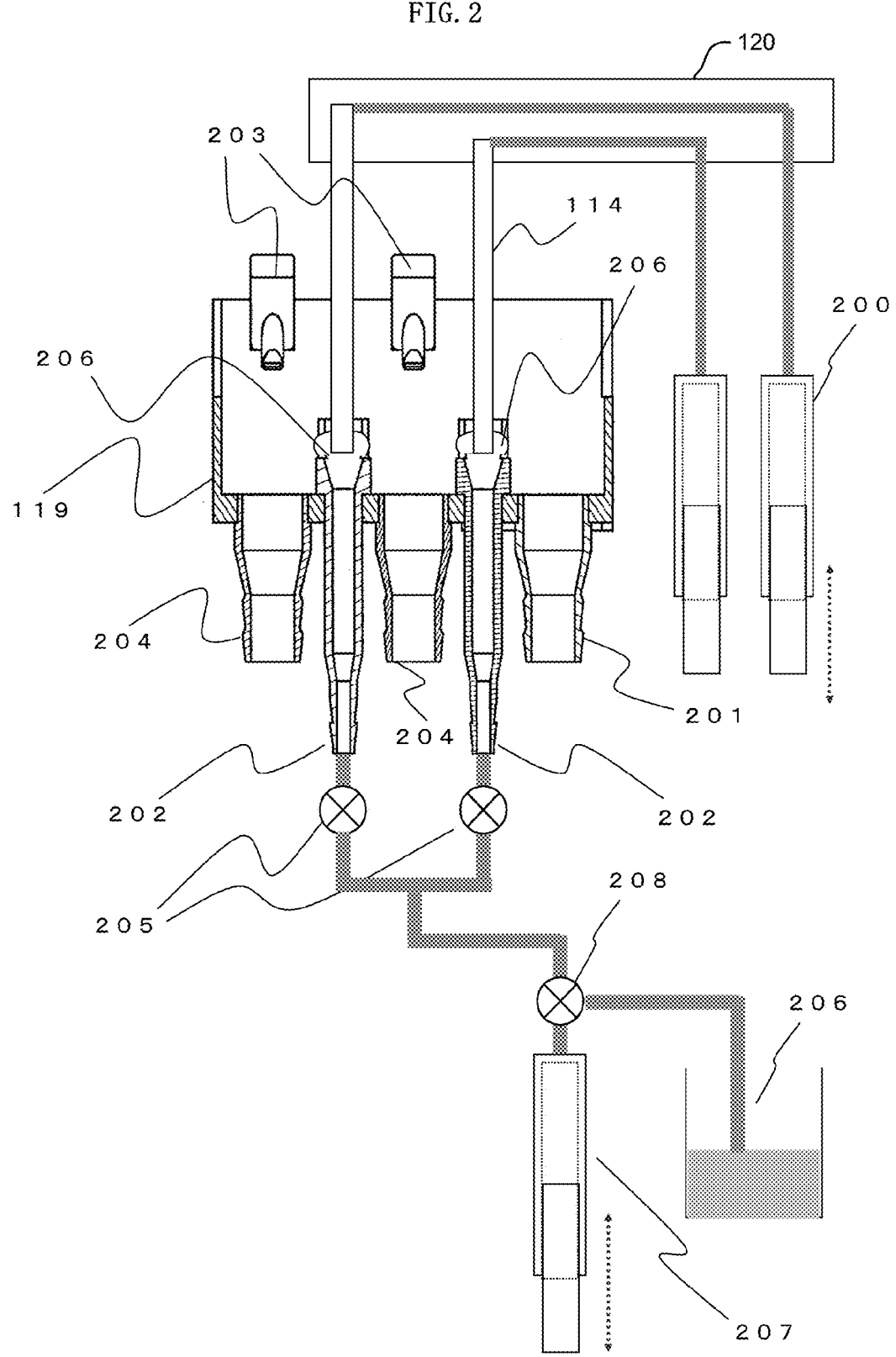
FIG. 2 illustrates a structure diagram of a dispensing nozzle of a reagent and of a rinse tank.

Referring to FIGS. 1 and 2 below, an embodiment of the present invention will now be described based on the basic structure of an automatic analyzer and analysis procedures.

First described is the overall structure of an automatic analyzer, one of the present embodiment. On the rack 101 of the automatic analyzer 100, sample vessels 102 containing a sample are placed. By a rack transfer line 117, the sample vessels move to a sample dispensing position adjacent to a sample dispensing nozzle 103.

An incubator disk 104 allows placement of multiple reaction vessels 105 and is capable of rotational movement to transfer each of the reaction vessels 105, which is arranged in a circumferential direction, to a particular position, respectively. A sample dispensing chip/reaction vessel transfer mechanism 106 is capable of moving in three directions, X, Y, and Z axes, and moves within the range of a sample dispensing chip/reaction vessel holding member 107, a reaction vessel stirring mechanism 108, a sample dispensing chip/reaction vessel disposal hole 109, a sample dispensing chip attachment position 110, and a given position of the incubator disk 104, thereby performing transfer of sample dispensing chips and reaction vessels. On the sample dispensing chip/reaction vessel holding member 107, unused reaction vessels 105 and sample dispensing chips are placed. The sample dispensing chip/reaction vessel transfer mechanism 106 moves to a position above the sample dispensing chip/reaction vessel holding member 107 and lowers itself to hold an unused reaction vessel and then moves upward. Thereafter, the sample dispensing chip/reaction vessel transfer mechanism 106 moves toward a position above a particular position of the incubator disk 104 and then moves downward to place the reaction vessel 105.

Next, the sample dispensing chip/reaction vessel transfer mechanism 106 moves to a position above the sample dispensing chip/reaction vessel holding member 107 and lowers itself to hold an unused sample dispensing chip and then moves upward. Thereafter, the sample dispensing chip/reaction vessel transfer mechanism 106 moves toward a position above the sample dispensing chip attachment position 110 and then moves downward to place the sample dispensing chip.

The sample dispensing nozzle 103 is capable of rotating and moving upward and downward and moves downward after moving to a position above the sample dispensing chip attachment position 110 to push the sample dispensing chip into the distal end of the sample dispensing nozzle 103 to attach it. Being attached with the sample dispensing chip, the sample dispensing nozzle 103 moves to a position above a sample vessel 102 placed on the transfer rack 101 and then moves downward to suction a given amount of the sample contained in the sample vessel 102. The sample dispensing nozzle 103 that has suctioned the sample moves to a position above the incubator disk 104 and then moves downward to discharge the sample into an unused sample vessel 105 held by the incubator disk 104. When the sample discharge is done, the sample dispensing nozzle 103 moves to a potion above the sample dispensing chip/reaction vessel disposal hole 109 to dispose of the used sample dispensing chip from the disposal hole.

On a reagent disk 111, multiple reagent vessels 118 are placed. A reagent disk cover 112 is placed on an upper portion of the reagent disk 111 so that the inside of the reagent disk 111 is maintained at a given temperature. On part of the reagent disk cover 112, a reagent disk cover opening 113 is provided. A reagent dispensing nozzle 114 can include a plurality of dispensing nozzles supported by a common arm 120 that is capable of rotating and moving upward and downward and moves downward after moving to a position above the opening 113 of the reagent disk cover 112 to insert the distal end of the reagent dispensing nozzle 114 into the reagent contained within a given reagent vessel to suction. a given amount of the reagent. Next, after moving upward, the reagent dispensing nozzle 114 rotates and moves to a position above a particular position of the incubator disk 104 to discharge the reagent into the reaction vessel 105.

The reaction vessel 105 into which the sample and reagent have been discharged moves to a particular position by the rotation of the incubator disk 104 and is then transferred to the reaction vessel stirring mechanism 108 by the sample dispensing chip/reaction vessel transfer mechanism 106. The reaction vessel stirring mechanism 108 stirs and mixes the sample and the reagent within the sample vessel by applying rotational movement to the reaction vessel. The reaction vessel that has completed the stirring is transferred back to a given position of the incubator disk 104 by the sample dispensing chip/reaction vessel transfer mechanism 106.

A detector unit reaction vessel transfer mechanism 115 is capable of rotating and moving upward and downward and moves to a position above a reaction vessel 105 for which sample-reagent stirring is done and a given amount of reaction time has passed at the incubator disk 104, in order to grab the reaction vessel 105 and transfer it to detector units 116 by rotational movement. Note that in the present embodiment, two detector units 116 and two detector unit reaction vessel transfer mechanisms 115 are provided, whereby parallel analysis is possible using the two detector units and doubling the efficiency of analysis processing can be achieved.

FIG. 2 is an external view of a rinse tank according to the present invention. In the present embodiment, a method for rinsing the reagent dispensing nozzle is described, but the same method can be applied to a method for rinsing a dispensing nozzle that dispenses blood, urine, and other samples. We first describe the structure of the rinse tank of the present embodiment.

A dispensing nozzle rinse tank 119 includes a remaining liquid outlet 201, first rinse liquid supply ports 202, second rinse liquid discharge ports 203, and second rinse liquid outlets 204. The remaining liquid outlet 201, the first rinse liquid supply ports 202, the second rinse liquid discharge ports 203, and the second rinse liquid outlets 204 exist at mutually close positions and are arranged according to the rinse procedures of dispensing nozzles. FIG. 2 is the case where two dispensing nozzles are rinsed, and when either one of the reagent dispensing nozzles 114 is located at the remaining liquid outlet 201, by the other being located at the second rinse liquid outlets 204, the second rinse liquid outlets 204 can serve the same function as the remaining liquid outlet 201.

In the case of a single reagent dispensing nozzle, there is a method to install a single first rinse liquid supply port 202, a single second rinse liquid supply port 203, and a second rinse liquid outlet 204. There is also a method to make the remaining liquid outlet 201 and the second rinse liquid outlets 204 as the same outlet port. When the number of reagent dispensing nozzles is not two but three or more, there is a method to install a single remaining liquid outlet 201, install at positions close to the remaining liquid outlet 201 as many rinse liquid supply ports as there are reagent dispensing nozzles, and install at positions close to the rinse liquid supply ports second rinse liquid supply ports 203 and second rinse liquid outlets 204.

The first rinse liquid supply ports 202 are supplied by a liquid sending syringe 207 from a first rinse liquid 206. The liquid sending syringe 207 is capable of supplying a given amount of the first rinse liquid 206. For example, there is a method to predetermine the kind of reagent to be suctioned and the reagent supply amount that corresponds to the dip amount of a dispensing nozzle with respect to the reagent when dispensation is performed by the dispensing nozzle and supply the predetermined rinse liquid amount with the liquid sending syringe 207 during a rinse that is to be performed after the reagent dispensing nozzle 114 has completed reagent dispensation.

As to the first rinse liquid 206, suctioning of the first rinse liquid 206 with a flow path switch valve 208 and supply of the first rinse liquid 206 to the first rinse liquid supply ports 202 are performed. When the first rinse liquid supply ports 202 exist at two or more locations, solenoid valves 205 exist between the flow path switch valve 208 and the first rinse liquid supply ports 202, and by opening the solenoid valve of the reagent dispensing nozzle to be rinsed, the reagent dispensing nozzle that requires a rinse can be rinsed.

Here, we describe the supply control of rinse liquid by a control method of the solenoid valves 205. When reagent dispensing nozzles are rinsed, the solenoid valves 205 open, and by the operation of the liquid sending syringe, a rinse liquid is supplied from the first rinse liquid supply ports 202. In FIG. 2, there are two reagent dispensing nozzles, and in a reagent dispensing operation, the two suction at the same time or only one of them suctions. When the two dispense at the same time, there is a method in which after a reagent is dispensed into a reaction vessel, the two reagent dispensing nozzles move to the first rinse liquid supply ports at the same time, and after opening the solenoid valves 205, by raising the liquid sending syringe 207, the rinse liquid is supplied to the two nozzles at the same time. Also, there is a method in which after moving to the first rinse liquid supply ports, by opening the solenoid valves one by one to supply a reagent with the liquid sending syringe, the first rinse liquid necessary for the reagent dispensing nozzles to suction is supplied. For example, referring to FIG. 2, after the solenoid valve that lies within the flow path of the first rinse liquid supply port 202 that lies at the right-side reagent dispensing nozzle is opened, the first rinse liquid is supplied with the liquid sending syringe 207. After the supply of the first rinse liquid, the solenoid valve 205 that lies within the flow path of the left-side rinse liquid supply port is opened, and the first rinse liquid is further supplied with the liquid sending syringe 207. Further, when a single nozzle is used for reagent dispensation, there is also a method in which only the solenoid valve that lies within the flow path of the second rinse liquid supply port of the reagent dispensing nozzle that has dispensed is opened, and the rinse liquid is supplied with the liquid sending syringe, thereby reducing consumption of the rinse liquid. It is to be noted that when three or more reagent dispensing nozzles 114 exist, the reagent dispensing nozzles can also be rinsed with the use of the above-described control method of the solenoid valves.

The second rinse liquid outlets 204 exist below the first rinse liquid supply ports 203 and perform discharge of the second rinse liquid. In FIG. 2, when the remaining liquid outlet 201 and the second rinse liquid outlets 204 communicate with the same outlet, the second rinse liquid outlet 204 that exists in the middle can also serve as a second rinse liquid outlet.

Next described is a method for rinsing a reagent dispensing nozzle. A reagent dispensing nozzle 114 is capable of rotating and moving upward and downward, and depending on the structure of the reagent dispensing nozzle 114, it is also capable of rotating and moving in horizontal directions. To suction a given reagent, the reagent dispensing nozzle 114 moves to a position above the opening 113 of the reagent disk cover 112, and the reagent disk 111 moves such that the reagent to be suctioned from the reagent dispensing nozzle 114 is located below the opening 113. After the reagent disk has moved the reagent to be suctioned to the opening, the reagent dispensing nozzle 114 moves downward. In this case, the downward movement of the reagent dispensing nozzle 114 is stopped by sensing such as liquid surface detection so that the dip section between the reagent dispensing nozzle 114 and the reagent is smaller. After the stop of the reagent dispensing nozzle 114, the reagent within the suction reagent vessel installed is suctioned by a reagent dispensing syringe 200 moving downward. After the completion of the suctioning, the reagent dispensing nozzle 114 moves upward and moves to a position above a reaction vessel 105 on the incubator disk 114 to perform discharge into the reaction vessel 105, followed by transfer to the reagent dispensing nozzle rinse tank 119.

Next, we describe a method for rinsing the reagent dispensing nozzle within the reagent dispensing nozzle rinse tank.

Figure 3:
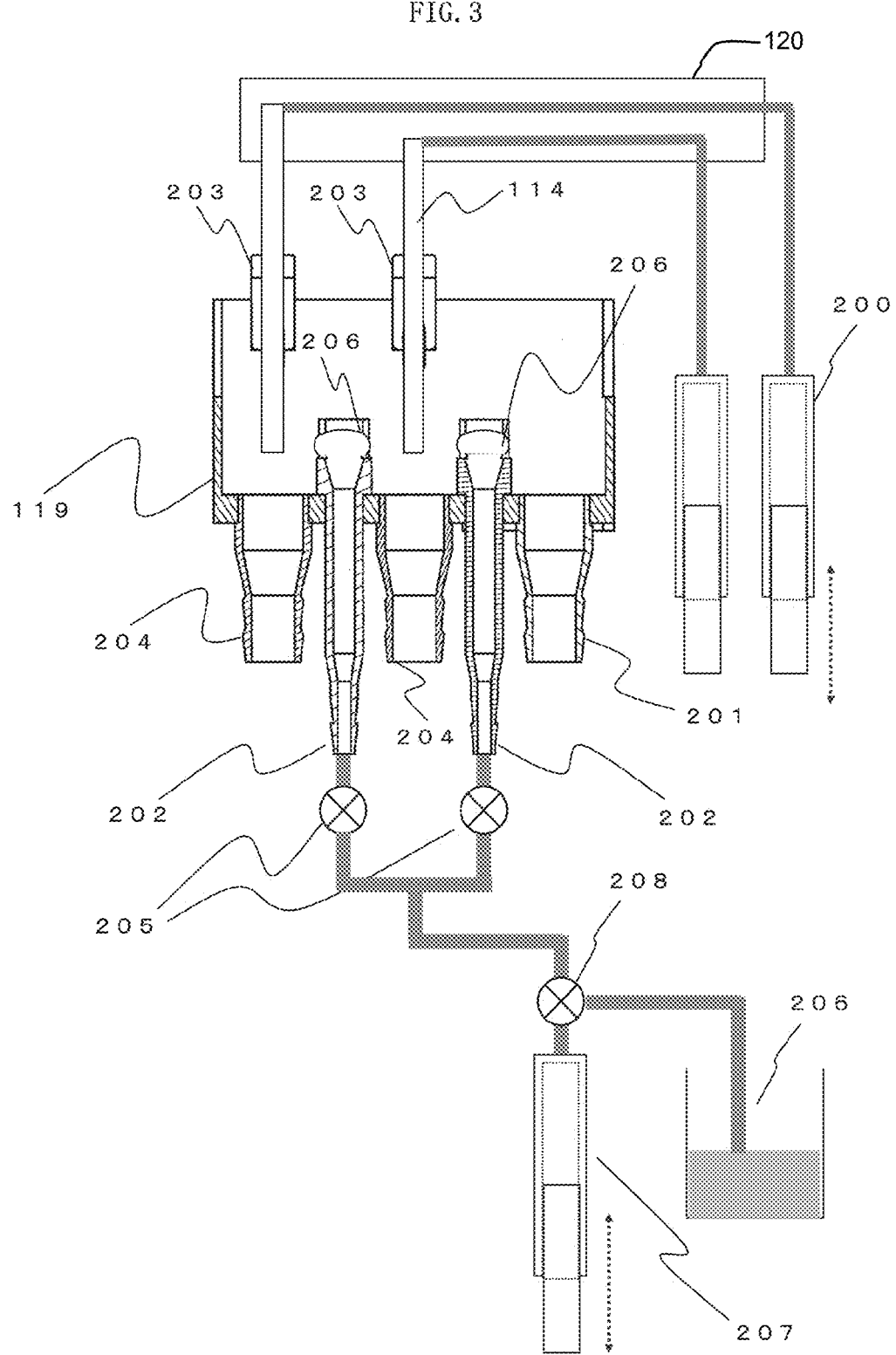
FIG. 3 illustrates the dispensing nozzles at the second rinse liquid discharge section.

After the discharge of the reagent into the reaction vessel 105, the reagent dispensing nozzle 114 moves to the remaining liquid discharge port 201 and then causes a reagent dispensing syringe 200 to move upward, thereby discharging all the reagent remaining within the nozzle. After the discharge of the reagent, the reagent dispensing nozzle 114 moves to the first rinse liquid supply port 202 located adjacent to the remaining liquid discharge port 201, as shown in FIG. 2. Because the first rinse liquid supply port 202 supplies the rinse liquid only to the reagent dispensing nozzle that has performed reagent dispensation by the above-describe control means of the solenoid valves 205 and the liquid sending syringe, only the reagent dispensing syringe 200 on the supplied rinse liquid side performs suctioning, thereby suctioning the rinse liquid into the reagent dispensing nozzle. After suctioning the rinse liquid into the reagent dispensing nozzle, the reagent dispensing nozzle 114 moves to a second rinse liquid outlet 203, as shown in FIG. 3. In this case, from the relative positional relationship between the first rinse liquid supply section and the second rinse liquid discharge section., the reagent dispensing nozzle can move from the first rinse liquid supply section to the second rinse liquid discharge section without moving upward or downward. After the transfer, the second rinse liquid is supplied from the second rinse liquid discharge port. 203 to rinse the outside of the reagent. dispensing nozzle. While the second rinse liquid is being supplied, by the reagent dispensing syringe moving upward and downward, all the rinse liquid that lies within. the reagent dispensing nozzle is discharged, and cleaning of the inside and outside of the reagent dispensing nozzle is completed, followed by repetitions of reagent suctioning and discharging again.

DESCRIPTION OF REFERENCE NUMERALS

100: Analyzer
101: Rack
102: Sample vessel
103: Sample dispensing nozzle
104: Incubator disk
105: Reaction vessel
106: Sample dispensing chip/reaction vessel transfer mechanism
107: Sample dispensing chip/reaction vessel holding member
108: Reaction vessel stirring mechanism
109: Sample dispensing chip/reaction vessel disposal hole
110: Sample dispensing chip attachment position
111: Reagent disk
112: Reagent disk cover
113: Reagent disk cover opening
114: Reagent dispensing nozzle
115: Reaction vessel transfer mechanism
116: Detector unit
117: Rack transfer line
118: Reagent vessel
119: Reagent dispensing nozzle rinse tank
200: Reagent dispensing syringe
201: Rinse liquid outlet
202: First rinse liquid supply port
203: Second rinse liquid discharge port
204: Second rinse liquid outlet
205: Solenoid valve 206: Rinse liquid
207: Liquid sending syringe
208: Flow path switch valve

The invention claimed is:

1. An automatic analyzer comprising:
a detector unit to analyze a reaction solution of a sample and a reagent;
a plurality of dispensing nozzles supported by a common arm where the nozzles are moved to dispense the sample or the reagent; and
a rinse tank for rinsing the dispensing nozzles, the rinse tank having a top and a bottom spaced from each other in a first direction,
wherein the rinse tank includes:
a plurality of first rinse liquid discharge ports arranged along the bottom of the rinse tank, each first rinse liquid discharge port being constructed to supply a first rinse liquid and facing the top of the rinse tank;
a plurality of second rinse liquid discharge ports arranged along the top of the rinse tank, each second rinse liquid discharge port being constructed to supply a second rinse liquid to flow to an exterior of one of the dispensing nozzles when aligned therewith,
wherein the first rinse liquid discharge ports are offset with respect to the second rinse liquid discharge ports in both the first direction and a second direction perpendicular to the first direction; and
a rinse liquid supply pipe connecting the first, rinse liquid discharge ports and a first rinse liquid supply, the rinse liquid supply pipe supplying the first rinse liquid for rinsing an inner wall of one of the dispensing nozzles from below,
wherein each dispensing nozzle is rinsed by moving from a first position aligned with one of the first rinse liquid discharge ports to a second position aligned with one of the second rinse liquid discharge ports, and
wherein the dispensing nozzles displace only in the second direction when moving from the corresponding first position to the corresponding second position.

2. The automatic analyzer of claim 1, wherein the rinse liquid supply pipe includes a valve, and wherein the analyzer includes a control mechanism that is programmed to control the valve such that the first rinse liquid is supplied from each first rinse liquid discharge port, at least while a corresponding one of the dispensing nozzles is aligned therewith.

3. The automatic analyzer of claim 1, further comprising:
a syringe constructed to draw liquid into and discharge liquid from one of the dispensing nozzles; and
a control mechanism programmed to:
move said one of the dispensing nozzles to the first position aligned with one of the first rinse liquid discharge ports,
control the syringe to draw a given amount of the first rinse liquid supplied from said one of the first rinse liquid discharge ports into said one of the dispensing nozzles,
move said one of the dispensing nozzles to the second position aligned with one of the second rinse liquid discharge ports, and
control the syringe to discharge the first rinse liquid in said one of the dispensing nozzles while the second rinse liquid from said one of the second rinse liquid discharge ports flows along an exterior of said one of the dispensing nozzles.

4. The automatic analyzer of claim 2, wherein the control mechanism is programmed to supply the first rinse liquid to any first rinse liquid discharge port and the second rinse liquid to any second rinse liquid discharge port so as to rinse only those of the plurality of dispensing nozzles that have dispensed the sample or the reagent.

5. The automatic analyzer of claim 1, wherein the analyzer includes a control mechanism that is programmed to control amounts of first rinse liquid supplied to the first rinse liquid discharge ports.

6. The automatic analyzer of claim 1, wherein distances along the first direction between adjacent ones of the plurality of first rinse liquid discharge ports are substantially equal to the distances along the first direction between adjacent ones of the plurality of dispensing nozzles.

7. The automatic analyzer of claim 5, wherein the control mechanism is programmed to control the amount of first rinse liquid to be supplied to each first rinse liquid discharge port based on a dip amount of a corresponding one of the dispensing nozzles.

8. The automatic analyzer of claim 1, wherein the first and second liquid discharge ports are alternately arranged along the second direction.

* * * * *